(12) United States Patent
Winge et al.

(10) Patent No.: US 6,423,830 B1
(45) Date of Patent: *Jul. 23, 2002

(54) PROCESS FOR PURIFYING APOLIPOPROTEIN A OR APOLIPOPROTEIN E

(75) Inventors: Stefan Winge, Stockholm; Sara Wiklund, Skarpnäck, both of (SE)

(73) Assignee: Esperion Therapeutics, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/617,898

(22) Filed: Jul. 17, 2000

Related U.S. Application Data

(63) Continuation of application No. 08/912,387, filed on Aug. 15, 1997, now Pat. No. 6,090,921.
(60) Provisional application No. 60/025,387, filed on Sep. 4, 1996.

(30) Foreign Application Priority Data

Aug. 23, 1996 (SE) ............................................. 9603068

(51) Int. Cl.$^7$ ............................ A61K 35/14; C07K 3/02
(52) U.S. Cl. ........................ 530/359; 530/380; 514/12
(58) Field of Search .............................. 530/359, 380; 514/12

(56) References Cited

U.S. PATENT DOCUMENTS

| | | | |
|---|---|---|---|
| 4,740,304 A | 4/1988 | Tierneid et al. .............. 210/639 |
| 5,059,528 A | 10/1991 | Bollan et al ................ 435/69.4 |
| 5,089,602 A | 2/1992 | Isliker et al. ................ 530/359 |
| 5,128,318 A | 7/1992 | Levine et al. ................... 514/12 |
| 5,834,596 A | 11/1998 | Ageland et al. ............... 514/12 |
| 6,090,921 A * | 7/2000 | Winge et al. ................ 530/359 |

FOREIGN PATENT DOCUMENTS

| | | |
|---|---|---|
| EP | 0 262 651 | 4/1988 |
| EP | 0 267 703 | 5/1988 |
| EP | 0 308 336 | 3/1989 |
| EP | 0 329 605 | 8/1989 |
| EP | 0 333 474 | 9/1989 |
| EP | 0 345 155 | 12/1989 |
| EP | 0 345 615 | 12/1989 |
| EP | 0 494 848 | 7/1992 |
| JP | 61096998 | 6/1986 |
| JP | 01095798 | 10/1987 |
| JP | 6228319 | 8/1994 |
| JP | 8003198 | 3/1996 |
| WO | WO 88/03166 | 5/1988 |
| WO | WO 90/12879 | 11/1990 |
| WO | WO 91/06655 | 5/1991 |
| WO | WO 93/12143 | 6/1993 |
| WO | WO 93/25561 | 12/1993 |
| WO | WO 94/13819 | 6/1994 |
| WO | WO 96/00237 | 1/1996 |
| WO | WO 96/04556 | 5/1996 |
| WO | WO 96/27608 | 9/1996 |

OTHER PUBLICATIONS

Mezdour et al., *Journal of Chromatography*, vol. 414, pp. 35–45, 1987.*

Alred et al., "Application of temperature–induced phase partioning at ambient temperature for enzyme purification," J Chromatoy A 669(2):289–98 (1994).

Alred et al., Synthesis of dye conjugates of ethylene oxide–propylene poplymers and application intemperature–induced phase partitioning, Bioseparation 2(6):363–73 (1992).

Alred, et al., "Partitioning of ecdysteriods using temperature–induced phase separation," J. Chromatography 628: 206–214 (1993).

Anspach, et al., "Removal of endotoxins by affinity sorbents," J. Chromatogr A 711(1): 81–92 (1986).

Badimon, et al., "Regression of antherosclerotic lesions by high density lipoprotein plasma fraction in the cholesterol–fed rabbit," J. Clin invest 85(4): 1234–41 (1990).

Berggren, et al., "Effects of salts and the surface hydrophobicity of proteins on partitioning in aqueous two–phase systems containing thermoseparating ethylene oxide–propylene oxide copolymers," J. Chromatography 718: 67–79 (1995).

Bradford, et al., "A rapid and sensitive method for the quantitation of microgram quantities of protein utilizing the principle of protein–dye binding," Anal Biochem72:248–54 (1976).

Brewer, et al., "The amino acid sequence of human apoa–i, an apollpoprotein oslated from high density lipoproteins," Biochem. Biophys. Res. Commun. 80(3):623–30 (1978).

Calebrisi, et al., "Molecular characterization of native and recombinant apolipoprotein A–IMilano dimer, The Introduction of an interchain disulfide bridge remarkably aters the physiochemical properties of apolipoprotein A–1," J Biol Chem 269(51): 32168–74 (1994).

(List continued on next page.)

Primary Examiner—Christopher S. F. Low
Assistant Examiner—Abdel A. Momamed
(74) Attorney, Agent, or Firm—Holland & Knight LLP

(57) ABSTRACT

The present invention relates to a process for purifying apolipoprotein A (ApoA) or apolipoprotein E (ApoE) from human plasma, by obtaining a fraction of human plasma containing said ApoA or ApoE, prepurifying said fraction in at least one step, binding said ApoA or ApoE to an anion-exchange chromatography gel, and thereafter eluting said ApoA or ApoE from said anion-exchange chromatography gel. The thus produced ApoA or ApoE can be used for the manufacture of a medicament in the treatment of atherosclerosis and cardiovascular diseases, or peripheral atherosclerosis and sepsis as well as in a method for treatment of atherosclerosis and cardiovascular diseases, or peripheral atherosclerosis and sepsis when administered in a therapeutically effective amount.

7 Claims, No Drawings

OTHER PUBLICATIONS

Cohn, et al., "Preparation and Properties of Serum and Plasma Proteins, IV. A System for the Separation into Fractions of the Protein and Lipoprotein Components of Biological Tissues and Fluids," J. Am, Chem. Soc. 68:459–475 (1946).

Deeb, et al., "A mutation in the human apolipoprotein A–1 gene, Dominent effect on the level and characteristics of plasma high density lipoproteins, " J. Biol. Chem. 266(21):13654–60 (1991).

*Dorland's Illustrated Medical Dictionary*(Twenty–fifth Edition) W.B. Saunders Publishers, 1974.

Eisenberg, et al., "A helical hydrophobic moment: a measure of the Amphiphilicity of a helix,"Nature 299: 371–374 (1982).

Emancipator, et al., "In vitro inactivation of bacterial endotoxin by human lipoproteins and apolipoproteins," Infectimmun 60(2):596–601 (1992).

Franceschini, et al., "Apolipoprotein Almilano. Accelarated binding and dissociation from lipids of a human apolipoprotein variant, " J Biol Chem 260(30): 16321–5 (1986).

Franceschini, et al., "High density lipoprotein –3 heterogensity in subjects with the apo–Almilano variant, " J. Biol. Chem, 257(17): 9926–30 (1982).

Franceschini, et al., "A–1Milano apoprotein, Decreassed high density lipoprotein cholesterol levels with significenat lipoprotein modifcations and without clinical atherosclerosis in an italian family," J. Clin. Invest. 66(6):892–900 (1980).

Freudenberg, et al., "Natural Toxins, *"Proc. Inc. Symp. Anim., Plant Microb, Toxins, 6hu th*ed. pp.349–354.

Gualandri, et al., "A1Milano apoprotein Identififcation of the complete kindred and evidence of a dominent genetic transmission, " Am. J. Hum. Genet. 37(6): 1083–97 (1985).

Harris, et al. "Enzyme purification using temperature–induced phase formation," Bioseparation 2(4):237–46 (1991).

Index, 11aEd., Merck and Co., Rahway NJ, pp. 342 and 455 (1989).

Isaachi, et al., "Mature apolipoprotein AI and its precureor proApoAI: Influence of the sequence at the 5' end of the gene on the efficiency of expression in *Escherchia coli.*" Gene 81(1):129–37 (1989).

Johansson, et al., "Effects of Salts on the Partition of Proteins in Aqueous Polymeric Biphasic Systems," Acts Chimice Scandivice B 2B:873–882 (1974).

Karplus, et al., "A new method for reduction of endotoxin contamination from protein solutions," J Immunol Methods 105(2):211–20 (1987).

Kistler, et al., "Large Scale Production of Human Plasma Fractions," Vox. Sang. 7:414–424 (1962).

Lerch, et al., "Isolation and properties of Apolipoprotein A for therapeutic use," Protidas Biol. Fluids 36:409–16 (1989).

Matsumae, et al., "Specific removal of endotoxin from protein solutions by Immobilized histidine," Biotechnol Appl Biochem 12(2):129–40 (1990).

Matsunaga, et al., "Apolipoprotein A–I deficiency due to a codon 84 nonsense mutation of the apolipoprotein A–I gene," Proc. Natl. Acad. Sci. U. S. A. 88(7):2793–7 (1991).

Mezdour, et al., "Anion–exchange fast protein liquid chromatographic characterization and purification of apolipoproteins A–I, A–II, C–I, C–III0, C–III1, C–III2 and E from human plasma," Journal of Chromatography 414:35–45 (1987).

Minobe, et al., "Characteristics and applications of adsorbents for pyrogen removal," Biotechnol Appl Biochem 10(2):143–53 (1981).

Moguilevsky, et al., "Production of human recombinant proapolipoprotein A–1 in *Escherichia coli*: purification and biochemical characterization," DNA B(6):429–36 (1989).

Munford, et al., "Binding of *Salmonella typhimurium* lipopolysaccharides to rat high–density lipoproteins," Infectimmun 34(3):835–43 (1988).

Nilsson, et al., "Immobilization and purification of enzymes with staphylococcal protein A gene fustion vectors," EMBO J. 4(4):1075–80 (1985).

O'Brien, et al., "Comparison of apolipoprotein and proteoglycan deposits in human coronary atherosclerotic plaques: colocalization of biglycan with apolipoproteins, "Circulation 98(6):519–27 (1998).

Oncley, et al. "The separation of the Antibodies, Isogglutinins, Prothrombin, Plasminogen and $\beta_1$–Lipoprotein into Subfractions of Human Plasma," J. Am. Chem. Soc. 71:541–550 (1948).

Peitsch, et al., "A purification method for apolipoprotein A–I and A–II," Analytical Biochemistry 178:301–05 (1989).

Pigiet, et al., "Thioredoxin–catalyzed refolding of disulfide –containing proteins," Proc Natl Acad Sci U S A. 83(20):7643–7 (1986).

Ross, et al., "Rapid Chromatographic Purification of Apolipoproteins A–I and A–II from Human Plasma," Analytical Biochem, 149:166–68 (1985).

Rubenstein, et al., "A new method for the fractionation of human plasma high density lipoprotein,,"Can. J. Biochem. 55(7):766–8 (1977).

Segrest, et al., "A molecular theory of lipid–protein interactions in the plasma lipoproteins," FEBS Lett. 38(3):247–58 (1974).

Sharma, et al., "Endotoxin detection and elimination in biotechnology," Biotechnol Appl Biochem. 8(1):5–22 (1986).

Sirtori, et al., "Human Apolipoproteins Mutants III," NATO ASI Series vol. 73 pp. 81–96 Springer Verlag: Berlin, 1993.

Soma, et al., "Recombinant apolipoproteins A–IMilano dimer inhibits carotid intimal thickening induced by pervascular manipulation in rabbits," Circ Res. 76(3):405–11 (1996).

Takada, et al., "Characterization of a new human apolipoprotein A–I Yeme by direct sequencing of polymerase chain reaction–amplified DNA," J. Lipid Res. 32(8):1275–80 (1991).

Tricerri, et al., "A rapid and efficient procedure for the purification of Human Apolipoprotein A–I using gel–filtration HPLC," IJBC 1:159–66 (1994).

Ulevitch, et al., "New function for high density lipoproteins, Isolation and characterization of a bacterial lipopolysaccharide–high density lipoprotein complex formed in rabbit plasma," J Clin Invest 67(3):827–37 (1981).

Walter, et al., Partitioning procedures and techniques: cells, organellas, and membranes," Methods Enzymol 228:42–63 (1994).

Weisgraber, et al., "Identification of the disulfide–linked homodimer of apolipoprotein E3 in plasma. Impact on receptor binding activity,"J Biol Chem 266(18):12029–34 (1991).

Weisgraber, et al., "Apolipoprotein A–I$_{Milano}$ Detection of normal A–I in affected subjects and evidence for a cysteine for arginine substitution in the variant A–I," J. Biol. Chem. 258(4):2508–13 (1983).

* cited by examiner

PROCESS FOR PURIFYING APOLIPOPROTEIN A OR APOLIPOPROTEIN E

CROSS-REFERENCE TO RELATED APPLICATIONS

This is a continuation of U.S. Ser. No. 08/912,387 filed Aug. 15, 1997, now U.S. Pat. No. 6,090,921, which claims priority from Provisional application Ser. No. 60/025,387, filed Sep. 4, 1996.

FIELD OF THE INVENTION

The present invention relates to a process for purifying apolipoprotein A (ApoA) or apolipoprotein E (ApoE), which are important components of the high density and low density lipoproteins in plasma. More particularly, this invention relates to a process for obtaining ApoA or ApoE from human plasma, by prepurifying said ApoA or ApoE in at least one step, binding said ApoA or ApoE to an anion-exchange chromatography gel, and thereafter eluting said ApoA or ApoE from said anion-exchange chromatography gel.

BACKGROUND OF THE INVENTION

The main function of lipoproteins in plasma is to transport lipids, such as cholesterol and triglycerides. For transport in plasma, cholesterol, normally as cholesteryl esters, and the triglycerides are included into lipoprotein particles in which they form a hydrophobic core. The core is surrounded by a surface coat containing phospholipids, unesterified cholesterol and proteins called apolipoproteins. The latter are responsible for the lipid transport, and in addition, some may interact with many of the enzymes involved in lipid metabolism. To date, at least nine apolipoproteins have been identified: A-I, A-II, A-IV, B, C-I, C-II, C-III, D and E.

There are four major classes of lipoproteins: chylomicrons (CM), very low density (VLDL), low density (LDL) and high density (HDL) lipoproteins. Of these, HDL is directly involved in the removal of cholesterol from peripheral tissues, carrying it back either to the liver or to other lipoproteins, by a mechanism known as "reverse cholesterol transport" (RCT).

The "protective" role of HDL has been confirmed in a number of studies. Recent studies directed to the protective mechanism(s) of HDL have been focused on apolipoprotein A-I (ApoA-I), the major component of HDL. High plasma levels of ApoA-I are associated with a reduced risk of CHD and presence of coronary lesions.

The apolipoprotein A-IMilano (ApoA-IM) is the first described molecular variant of human ApoA-I (Franceschini et al. (1980) J. Clin. Invest. 66: 892–900). It is characterized by the substitution of Arg 173 with Cys 173 (Weisgraber et al. (1983) J. Biol. Chem. 258: 2508–2513). The mutant apolipoprotein is transmitted as an autosomal dominant trait and 8 generations of carriers have been identified (Gualandri et al. (1984) Am. J. Hum. Genet. 37: 1083–1097). The status of a ApoA-IM carrier individual is characterized by a remarkable reduction in HDL-cholesterol level. In spite of this, the affected subjects do not apparently show any increased risk of arterial disease. Indeed, by examination of the genealogical tree it appears that these subjects may be "protected" from atherosclerosis.

Apolipoprotein E (ApoE) is a ligand for the LDL receptor. As a result, ApoE plays an important role in cholesterol metabolism. In addition, ApoE is involved in the hepatic clearance of chylomicron remnants.

Several methods have been proposed for purifying ApoA and ApoE from plasma. One of the most common ways to purify apolipoprotein A-I is to use ultracentrifugation in order to isolate high density lipoproteins (HDL) followed by a separation of Apo A-I from the HDL-particle. There are several different ways to purify Apo A-I from HDL, including solvent extraction. Ultracentrifugation is a very time-consuming method and it is not suitable for large scale isolation. Methods using plasma as starting material and which do not include ultracentrifugation have been described, for example chromatographic purification (Ross S. E. et al, Rapid chromatographic purification of apolipoproteins A-I and A-II from human plasma, Analytical Biochemistry 149, p. 166–168 (1985)), and purification using gel-filtration HPLC (Tricerri A. et al, A rapid and efficient procedure for the purification of human apolipoprotein A-I using gel-filtration HPLC, IJBC, 1, p. 159–166 (1994)). Other methods which use fractions from cold ethanol fractionation as starting material have also been published (Peitsch et al, A purification method for apolipoprotein A-I and A-II, Analytical Biochemistry, 178. p. 301–305 (1989)).

EP-A0329 605 to Rotkreuzstiftung Zentrallaboratorium Blutspendedienst SRK and Lerch et al, Isolation and properties of apolipoprotein A for therapeutic use, Protides Biol. Fluids, 36, p. 409–416 (1989), relate to preparation of Apolipoproteins from fractions of human blood plasma containing lipoproteins. EP-A-0329 605 and Lerch et al disclose that precipitate B and IV of a cold ethanol fractionation process can be used as starting material for producing ApoA. Use is made of buffers containing unusually high ethanol concentrations (68–96% ethanol), optionally with an organic solvent, for precipitating contaminants. The precipitates are solubilized mn guanidine hydrochloride, which is subsequently removed by gel filtration. An anion-exchange chromatography step is included to bind the contaminants, while the ApoA passes through.

JP-A-08003198 to Chemo-Sero-Therapeutics Research Institute relates to preparation of Apolipoprotein A-I from human plasma by incubating apolipoprotein A-I containing plasma with A lower aliphatic alcohol, centrifuging the culture mixture obtained, and applying the resulting supernatant to a hydrophobic chromatography resin in the presence of a lower aliphatic alcohol.

WO-A-93/12143 to Pharmacia & Upjohn (formerly Kabi Pharmacia AB) relates to preparation of the dimer of Apolipoprotein A-IM from blood plasma collected from Apo A-IM carriers as well as from solutions containing Apolipoprotein A-IM produced by recombinant DNA techniques. The dimers can be produced from blood plasma by isolating the high density lipoproteins (HDL) particles and separating the dimer by use of one or more gel filtration steps, or by purifying the monomers on Thiopropyl-SEPHAROSE® and thereafter converting said monomers to the dimers.

There are presently several methods known for purifying plasma-derived ApoA and ApoE. There is, however, a need for an additional quick, sensitive and reliable method for preparation of plasma-derived ApoA and ApoE on a pilot-plant and industrial scale. It is the purpose of the present invention to provide such a method.

SUMMARY OF THE INVENTION

The present invention relates to a process for purifying apolipoprotein A (ApoA) or apolipoprotein E (ApoE) from human plasma, by obtaining a fraction of human plasma containing said ApoA or ApoE, prepurifying said fraction in at least one step, binding said ApoA or ApoE to an anion-exchange chromatography gel, and thereafter eluting said ApoA or ApoE from said anion-exchange chromatography gel. The thus produced ApoA or ApoE can be used for the manufacture of a medicament in the treatment of atherosclerosis and cardiovascular diseases, or peripheral atherosclerosis and sepsis as well as in a method for treatment of atherosclerosis and cardiovascular diseases, or peripheral atherosclerosis and sepsis when administered in a therapeutically effective amount.

DETAILED DESCRIPTION OF THE INVENTION

An object of the present invention is to provide an efficient purifying process for producing ApoA or ApoE from plasma with a low enough content of impurities to obviate the need for further purifying steps.

A further object of the present invention is a process providing a high yield of plasma-derived ApoA or ApoE, i.e. a process with a minimal loss of product.

Another object of the present invention is to provide an efficient process, where the biological activity of plasma-derived ApoA or ApoE is essentially retained.

Still another object of the present invention is to provide a purified ApoA or ApoE from Cohn's fraction IV.

The objects above are met by the present invention, which relates to a process for purifying apolipoprotein A (ApoA) or apolipoprotein E (ApoE) from human plasma, by obtaining a fraction of human plasma containing said ApoA or ApoE, prepurifying said fraction in at least one step, binding said ApoA or ApoE to an anion-exchange chromatography gel, and thereafter eluting said ApoA or ApoE from said anion-exchange chromatography gel.

Anion-exchange chromatography where ApoA or ApoE is bound to the gel preceded by prepurification in at least one step provides another dimension for purifying ApoA or ApoE derived from human plasma, since additional separation criteria are utilized compared to those already used. Thus, a substantial amount of impurities, such as various proteins, can be made to pass through the anion-exchange chromatography gel, while ApoA or ApoE remain bound to the gel surface. This is quite surprising, since conventionally, if an anion-exchange chromatography step is utilized, the impurities are bound to the gel while ApoA or ApoE passes through the anion-exchange gel. With the present invention, ApoA and ApoE can be simply and efficiently separated from the impurities found in various fractions of human plasma, thereby providing an apolipoprotein with a purity in excess of 95%.

The present invention also relates to use of ApoA or ApoE produced according to the inventive process for the manufacture of a medicament comprising the ApoA or ApoE in the treatment of atherosclerosis and cardiovascular diseases, or peripheral atherosclerosis and sepsis.

The present invention further relates to a method for treatment of atherosclerosis and cardiovascular diseases, or peripheral atherosclerosis and sepsis by administering ApoA or ApoE produced according to the inventive process in a therapeutically effective amount.

The valuable components of human plasma, mainly proteins, can be separated by various fractionation methods, e.g. cold ethanol fractionation such as the Cohn or Cohn-Oncley process (Cohn et al, J. Am. Chem. Soc. 68, p. 459–475 (1946) and Oncley et al, J. Am. Chem. Soc. 71, p. 541–550 (1949)). Plasma fractions suitable for use in the present invention can be also be produced by variants of this original process, e.g. the Kistler-Nitschmann process (Nitschmann et al, Helv. Chim. Acta 37, p. 866–873 (1954) and Kistler et al, Vox Sang. 7, p. 414–424 (1962)). The cold ethanol fractionation processes, such as the Cohn process, are based on the simple principle that certain proteins are made insoluble in each step of the fractionation. These precipitated proteins can be separated from the rest of the solution through e.g. sedimentation, centrifugation or filtration. In the cold ethanol fractionation processes, ethanol is used for making the proteins precipitable at low temperatures. Typically, the ethanol concentration is gradually increased from 0% (w/w) up to 40% (w/w) and the temperature varied between 0° C. and −10° C. The result of the process is at least five different fractions, designated I to V.

Fractions of human plasma suitable for use in the present invention can be any fraction containing ApoA or ApoE, including cryo and serum. Human serum is a supernatant obtained by increasing the ethanol concentration to about 8% (w/w), thereby precipitating fraction I containing e.g. fibrinogen. Fractions II+III, obtained by increasing the ethanol concentration to about 25% (w/w) can also be used. It is, however, preferred to use a fraction obtained by increasing the ethanol concentration to about 38 up to about 42% (w/w), preferably about 40% (w/w). If the conventional Cohn process is used, such an alcoholic solution of human plasma is denoted Cohn's fraction IV.

The temperature of the fractions of human plasma suitable for use in the present invention can be in the range of from −10° C. up to 0° C., suitably in the range of from −8° C. up to −2° C. The pH of the fractions of human plasma, suitable for use in the present invention can be in the range of from 5 up to 7, preferably in the range of from 5.5 up to 6.5.

Apart from ethanol, other lower aliphatic alcohols are conceivable for use in the cold fractionation. Thus, use can be made of any straight or branched alcohol with one to six carbon atoms. It is, however, preferred that the alcohol is methanol, ethanol, n-propanol or isopropanol, n-butanol, sec-butanol, isobutanol or tert-butanol, more preferably ethanol.

The proteins of human plasma can be gradually precipitated also by use of other chemical substances. Thus, apart from lower aliphatic alcohols, ethers, ammonium sulfate, rivanol (2-ethyl-6-9-diamine acridinelactat) and various polyethylene glycols can be used to advantage for obtaining fractions rich in ApoA or ApoE, and therefore suitable for use as starting materials in the present invention.

The matrix of the anion-exchange chromatography gel can be selected from various hydrophilic matrices e.g. agarose matrices such as a wide variety of SEPHAROSE® matrices sold by Pharmacia Biotech of Uppsala, Sweden, organic polymer matrices such as TSK-gels sold by Tosoh Corp. of Tokyo, Japan, or highly porous organic polymer matrices sold by Per Septive Bio-systems of Boston, USA. The matrix is preferably an agarose matrix. Suitable agarose matrices in the present invention are, apart from SEPHAROSE®, MINILEAK® sold by Kem-En-Tec A/S of Copenhagen, Denmark and Bio-Gel A sold by Bio-Rad, of Brussels, Belgium. Preferably, the matrix is cross-inked allowing for a fast flow (FF) and thereby high production capacity.

The matrices of the present invention can be soluble or insoluble in various common solvents, e.g. organic polymers soluble or insoluble in water with or without ethanol. Matrices also include e.g. filters to which anionic ligands have been coupled.

Anion-exchange chromatography gels useful in the present process are e.g. DEAE agarose gels, especially DEAE-SEPHAROSE®, and Q agarose gels, especially Q-SEPHAROSE®, both types sold by Pharmacia Biotech of Uppsala, Sweden. Further examples of anion-exchange gels that can be used in the present process are Super Q-650 and Fractogel EMD DEAE-650 sold by Toso Haas of Tokyo, Japan, and DSAE Hyper D or Q Hyper D sold by Biosepra S. A. of France. More preferably, the anion-exchange matrix is DEAE-SEPHAROSE® FF.

The ionic strength of the buffer used to equilibrate the anion-exchange gel before applying an aqueous solution containing ApoA or ApoE to said gel as well as the ionic strength of said ApoA or ApoE solution can be in the range of from about 0.01 up to about 10 mS/cm, suitably in the range of from 0.1 up to 6 mS/cm, and preferably in the range of from 0.5 up to 4 mS/cm.

The concentration of total protein in the aqueous solution applied to the anion-exchange gel can be measured by absorption at 280 nmi($A_{280}$). Using this measure, the concentration of total protein in the aqueous solution applied to the anion-exchange gel can be in the range of from about 0.01 $A_{280}$ units up to about 100 $A_{280}$ units, suitably in the range of from 0.1 up to 50 $A_{280}$ units, and preferably in the range of from 0.5 up to 10 $A_{280}$ units.

To achieve high capacity on high-resolution chromatography steps, such as anion-exchange chromatography steps, the starting material has to be as pure as possible, Therefore, the present process involves at least one step for prepurifying the fraction containing ApoA or ApoE for increasing the purity of the ApoA or ApoE before the anon-exchange chromatography step.

If the ApoA or ApoE-containing fraction of human plasma contains precipitates, and in particular if the precipitates contain ApoA or ApoE, it is preferred to prepurify said fraction by separating the precipitates from the liquid, e.g. by filtration, centrifugation or sedimentation, to obtain a stating material rich in ApoA or ApoE. It is suitable to use filtration, preferably in the presence of a filter aid which facilitates the passage of the liquid through the filter. The filter aid can be of various origin, e.g. granules of inorganic material such as $SiO_2$ or an organic polymer, of one or more sizes, in optional mixture andlor sequence. The inorganic material may contain at least 70% of $SiO_2$, suitably at least 80% of $SiO_2$, and preferably at least 90% of $SiO_2$. Suitable examples include CELITE™ 560, with a median particle size in the range of from about 40 up to about 70 $\mu$m, suitably in the range of from 50 up to 60 $\mu$m, and HYFLO™ Super-Cel, with a median particle size in the range of from about 10 up to about 35 $\mu$m, suitably in the range of from 15 up to 25 $\mu$m. CELITE™ 560 and HYFLO™ Super-Cel contains 89.6% of $SiO_2$, 4.0% of $Al_2O_3$ and 1.3–1.5% of $Fe_2O_3$. CELITE™ 560 and HYFLO™ Super-Cel are marketed by Celite Corp. a World Minerals Inc. of Lompoc, Calif. in the U.S. Preferably, HYFLO™ Super-Cel is used in a mixture with CELITE™ 560, wherein HYFLO™ Super-Cel is added before CELITE™ 560.

In a suitable embodiment of the present invention, a washing solution is used to remove macromolecular impurities, such as proteins, from precipitated ApoA or ApoE, preferably in the presence of a filter aid, to obtain a precipitate of high specific activity for flier processing. Thus, by selecting suitable conditions in the washing step it is possible to make the ApoA or ApoE stay on the filter aid, while the impurities are dissolved and washed away. The washing solution may be water or a washing buffer, preferably a washing buffer. The washing buffer may contain organic acids, such as citric acid or sodium acetate, suitably citric acid. The washing buffer may also contain inorganic compounds, such as phosphates, suitably disodiumhydrogenphosphate. A combination of citric acid and disodiumhydrogenphosphate is preferred.

The temperature of the washing solution can be in the range of from about 0° C. up to about 90° C., suitably in the range of from 1° C. up to 50° C., and preferably in the range of from 2° C. up to 10° C.

After adding the washing solution to remove impurities from precipitated ApoA or ApoE, the resulting aqueous solution is mixed for a period of time in the range of from about 15 min up to about 10 hours, suitably from 1 hour up to 5 hours. After mixing, the dissolved impurities are allowed to separate from solid ApoA or ApoE, e.g. by sedimentation, for a period of time in the range of from about 5 min up to about 5 hours, suitably from 15 min up to 3 hours.

If ApoA or ApoE mainly exist as a precipitate in the fraction of human plasma used as the starting material for the present process, it is suitable to solubilize the precipitated ApoA or ApoE separated e.g. by filtration, centrifugation or sedimentation, in an extraction buffer. The extraction buffer should contain a compound capable of essentially disrupting, suitably completely disrupting, protein-protein interactions, e.g. a surfactant or a compound containing two or three nitrogen atoms bonded to a carbon atom, or a mixture thereof. Suitably, a compound containing two or three nitrogen atoms bonded to a carbon atom is used for solubilizing precipitated ApoA or ApoE separated in a filtration step, preferably after a washing step used to remove impurities.

The compound containing two or three nitrogen atoms bonded to a carbon atom is suitably selected from the group consisting of urea, arginine, guanidine hydrochloride, benzamidine and mixtures thereof, preferably urea.

Examples of surfactants which can be used to advantage to solubilize the precipitated ApoA or ApoE in the present invention are various bile acids and esters and salts thereof, such as deoxycholic acid, deoxycholates, cholic acid and cholates. Specific examples include sodium deoxycholate and sodium cholate. Also, non-ionic surfactants, e.g. zero-net-charge surfactants such as polyoxyethylene sorbitan fatty esters, block co-polymers and alkyl ethoxylates, can be used to advantage in the present invention. Examples of polyoxyethylene sorbitan fatty esters are polyoxy-ethylene-(20)-sorbitan monolaurate, e.g. TWEEN® 80, and polyoxy-ethylene-(20)-sorbitan monooleate, e.g. TWEEN® 20, both sold by ICI of Great Britain. Examples of the block co-polymers are combinations of polypropyleneglycol and polyethyleneglycol, e.g. PLURONIC® sold by BASF in Germany. Examples of alkyl ethoxylates are TRITON® X-100 and TRITON® X-114 sold by Union Carbide in USA.

The concentration of the compound containing two or three nitrogen atoms bonded to a carbon atom can be in the range of from about 0.5 M up to saturation at the prevailing conditions, suitably in the range of from 1 M up to 8 M, and preferably in tie range of from 3 M up to 7 M.

It lies within the competence of the skilled person to arrive at a suitable concentration for surfactants used to solubilize the precipitated ApoA or ApoE.

The temperature of the extraction buffer can be in the range of from about 0° C. up to about 90° C., suitably in the range of from 2° C. up to 50° C., and preferably in the range of from 4° C. up to 20° C.

After adding the surfactant or compound containing two or three nitrogen atoms bonded to a carbon atom to solubilize ApoA or ApoE, the resulting aqueous solution is mixed for a period of time in the range of from about 15 min up to about 10 hours, suitably from 1 hour up to 5 hours. After mixing, the resulting precipitates are allowed to separate from the liquid, e.g. by sedimentation, for a period of time in the range of from about 5 min up to about 5 hours, suitably from 15 min up to 3 hours.

In a preferred embodiment of the present invention, the fraction containing ApoA or ApoE is prepurified by filtering for recovering precipitated ApoA or ApoE, washing for removing impurities from said precipitated ApoA or ApoE, and thereafter solubilizing the washed ApoA or ApoE.

In another embodiment of the present invention, the fraction containing ApoA or ApoE is prepurified by adding a compound enhancing precipitation of especially high-molecular weight proteins and fatty compounds. In this way, the impurities, mainly other plasma proteins, can be precipitated while ApoA or ApoE remain essentially dissolved. Suitable examples of such precipitation enhancers include a wide variety of polyethylene glycols (PEG), e.g. PEG 4000 marketed by Merck & Co., Inc. of New Jersey, USA, ammonium sulfate and rivanol (2-ethyl-6-9-diamine acridinelactat).

A particularly preferred embodiment of the present invention, comprises obtaining a fraction of human plasma containing ApoA or ApoE, prepurifying said fraction by filtering for recovering precipitated ApoA or ApoE, washing for removing impurities from said precipitated ApoA or ApoE, thereafter solubilizing the washed ApoA or ApoE, and subsequently adding a compound enhancing precipitation of especially high-molecular weight proteins and fatty compounds.

The concentration of the precipitation enhancer can be in the range of from about 1% (w/w) up to about 50% (w/w), suitably in the range of from 3 up to 20% (w/w), and preferably in the range of from 5 up to 15% (w/w).

After adding the precipitation enhancer, the resulting aqueous solution is mixed for a period of time in the range of from about 10 min up to about 5 hours, suitably from 30 min up to 3 hours.

The temperature in the resulting aqueous solution obtained in the precipitation step can be in the range of from about 0° C. up to 50° C., suitably in the range of from 2° C. up to 15° C.

The pH of the washing buffer, the extraction buffer, and the aqueous solution resulting from the precipitation step can be in the range of from about 2 up to about 10, preferably in the range of from 3 up to 7.

The precipitated impurities may be removed by methods conventional per se, e.g. centrifugation, filtration or sedimentation, separately or in a sequence. Suitably, in the present process sequence, use is made of centrifugation followed by filtration.

In one embodiment of the present invention, an aqueous solution containing ApoA or ApoE eluted from the anion-exchange chromatography gel is subsequently applied to a gel-filtration gel capable of separating a mixture of macromolecules and equilibrated with a compound capable of reducing, suitably essentially disrupting and preferably completely disrupting, protein-protein interactions.

The gel-filtration step may follow immediately after the anion-exchange chromatography step. It lies, however, within the scope of the present invention to make use of one or more intermediate process steps, for example ultrafiltration or diafiltration.

The gel-filtration gels of the present invention relate to gets capable of separating a mixture of macromolecules from each other. Gels intended for buffer exchange or desalting, e.g. SEPHADEX® G25, are not suitable for use in the present invention. More particularly, the gel-filtration gels of the present invention should be capable of separating a mixture of macromolecules, especially proteins and polypeptides, with a molecular mass in the range of from about 10,000 Da up to about 600,000 Da. Suitably, the gel-filtration gels of the present invention are capable of separating a mixture of macromolecules with a molecular mass in the range of from 15,000 Da up to 450,000 Da, and preferably in the range of from 20,000 Da up to 300,000 Da.

The matrix of the gel-filtration gel can be selected from a wide variety of matrices such as agarose matrices. Preferred agarose matrices are highly crosslinked agarose matrices such as SUPERDEX®, SUPEROSE® and SEPHACRYL® matrices sold by Pharmacia Biotech of Uppsala, Sweden. The matrix of the gel-filtration gel can be selected also from e.g. TSK-gels and Toyopearl and Fractogel matrices sold by Tosoh Corp. of Tokyo, Japan. Suitable gel-filtration gets include SUPERDEX®, SUPEROSE® 6, SUPEROSE® 12, TSK-gel G 300 SW, Toyopearl HW-55 and Toyopearl HW-65.

In the embodiment where a gel-filtration gel step is used after the anion-exchange chromatography gel step, it is a prerequisite that the butter used for equilibrating and eluting the gel-filtration gel contains a compound capable of reducing, suitably essentially disrupting, and preferably completely disrupting protein-protein interactions before applying the ApoA or ApoE solution. A compound capable of essentially disrupting protein-protein interactions tend to disrupt nearly all non-covalent interactions in and between native proteins, such as ApoA or ApoE. The presence of a compound capable of reducing or, even better, disrupting protein-protein interactions in the equilibration buffer, therefore, facilitates separation of ApoA or ApoE from the remaining impurities.

The compound capable of reducing or disrupting protein-protein interactions can be e.g. surfactants, especially anionic ones, and compounds exhibiting a chaotropic effect, such as compounds containing two or three nitrogen atoms bonded to a carbon atom. The ability of a compound, e.g. a salt, to make a solvent, e.g. water, less polar is called the chaotropic effect. The compound containing two or three nitrogen atoms bonded to a carbon atom is suitably selected from the group consisting of urea, arginine, guanidine hydrochloride, benzamidine and mixtures thereof, preferably urea. The compound capable of reducing or disrupting protein-protein interactions is suitably an anionic surfactant, preferably sodium dodecyl sulfate (SDS).

Many ionic surfactants will exhibit anionic or cationic overall charge, depending especially upon pH, temperature and ionic strength of the solution at issue. Therefore, many surfactants may be used to advantage in the present invention by selecting a suitable combination of pH, temperature and ionic strength of the equilibration buffer.

Examples of surfactants which can be used to advantage in the present invention include bile acids and salts and esters thereof, such as deoxycholic acid, deoxycholates, cholic acid and cholates. Specific examples include sodium deoxycholate and sodium cholate. Reference is here made to the Merck Index, 11th ed., Merck & Co., Inc., Rahway, N.J., USA, p. 342 and 455 (1989).

In the present invention, surfactant also includes various lipids, which can be natural or synthetic compounds consisting of acyl carriers, such as glycerides, sphingosine, cholesterol, or derivatives or mixtures thereof, to which one or more fatty acids can be bonded. The lipids can, depending on their polarity, be divided into non-polar, polar and amphiphilic lipids. Examples of non-polar lipids are monoacylglycerides, diacylglycerides, triacylglycerides, and cholesterol. Examples of polar and amphiphilic lipids are phospholipids and glycolipids. Suitably, the polar and amphiphilic lipids are bilayer forming, such as phosphatidylcholine (PC), phosphatidylinositol (PI), phosphatidylglycerol, phosphatidyletanolamine, phosphatidylserine, sphingomyelin, or mixtures thereof. The natural lipids can be produced from e.g. soybean oil, maize oil, soy lecithin and egg lecithin. Other suitable examples are synthetic and saturated or unsaturated PC:s, such as dipalmitoyl phosphatidylcholine (DPPC) and dimyristyl phosphatidylcholine (DMPC).

The concentration of a compound capable of reducing or disrupting protein-protein interactions in the buffer used for equilibrating the gel-filtration gel can be in the range of from about 0.001 up to about 10% (w/w), suitably in the range of from 0.005 up to 2% (w/w). The concentration of a compound capable of reducing or disrupting protein-protein interactions is preferably in the range of from 0.01 up to 0.5% (w/w).

The concentration of total protein in the aqueous solution applied to the gel-filtration gel can be measured by absorption at 280 nm ($A_{280}$). Using this measure, the concentration of total protein in the aqueous solution applied to the gel-filtration gel can be in the range of from about 0.1 $A_{280}$ units up to about 100 $A_{280}$ units, suitably in the range of from 1 up to 40 $A_{280}$ units, and preferably in the range of from 5 up to 15 $A_{280}$ units.

The pH of the buffer used for equilibrating the gel-filtration gel is suitably in the range of from about 2 up to about 10, and preferably in the range of from 5 up to 8.

The temperature of the buffer used for equilibrating the gel-filtration gel and of the aqueous solution containing ApoA or ApoE applied to the gel-filtration gel can be in the range of from about 0 up to about 90° C., suitably in the range of from 10 up to 50° C., and preferably in the range of from 20 up to 30° C.

The total ionic strength of the elution buffer from the gel-filtration gel can be in the range of from about 0.01 up to about 150 mS/cm, suitably from 0.5 up to 50 mS/cm, and preferably from 5 up to 15 mS/cm.

In the present invention, the gel-filtration step may follow immediately after the anion-exchange chromatography step. It lies, however, within the scope of the present invention to make use of one or more intermediate process steps, for example ultrafiltration.

In the present invention, the anion-exchange chromatography step can be repeated, to give totally two, three or even more anion-exchange steps in a purification sequence. The same is valid for the prepurifying step as well as the gel-filtration step. The use of several anion-exchange steps, several prepurifying steps and/or several gel-filtration steps can reduce the content of impurities further, and at the same time increase the concentration of ApoA or ApoE. These and other advantages, of course, have to be weighed against the increase in apparatus costs. If at least two anion-exchange steps are used, they can be used with or without intermediate process steps.

The ApoA or ApoE obtained by the present process are suitably treated to inactivate or preferably, remove, any virus present. A suitable method for removing the viruses is the virus-filtering method disclosed in WO-A-96/00237 to Pharmacia & Upjohn AB (formerly Pharmacia AB), which is hereby incorporated by reference.

Each process step can be continuous, e.g. performed on a column, or batchwise.

Apart from the starting material of the present invention, i.e. the fraction of human plasma containing ApoA or ApoE, the aqueous solutions of the present invention should contain less than about 30% (w/w) of alcohol. Suitably, the aqueous solutions contain less than 10% (w/w) of alcohol, and preferably less than 5% (w/w) of alcohol. More preferably, the aqueous solutions of the present invention are essentially free of alcohol. The alcohol is conventionally ethanol, but can also be one or more other lower aliphatic alcohol, e.g. those mentioned in connection with the cold fractionation.

The present invention is used for purifying any apolipoprotein A (ApoA) or apolipoprotein E (ApoE), or analogs thereof, obtained from human plasma.

In the present invention, an analog of ApoA or ApoE is defined as a poly-peptide having an amino acid sequence substantially identical to that of naturally occurring ApoA or ApoE but differing from it by the addition, deletion or substitution of one or more amino acids while retaining the biological activity of naturally occurring ApoA or ApoE.

In the present invention, the terms ApoA and ApoE include any preform or fragment, or any truncated, extended or mutated form. Preform relates e.g. to the 249 amino acid Met form of ApoA-I as disclosed in WO-A-88/03166 assigned to Sirtori et al. Other preforms are the proapolipoprotein A-I's disclosed in U.S. Pat. No. 5,059,528 to UCB as well as EP-A-308336, JP 216988/1984 and JP 252048/1987 all to Mitsubishi Chem. Ind. Fragment relates to a part of ApoA or ApoE containing at least one α-helix, e.g. as disclosed in WO-A-93/25581 assigned to Innogenetics S.A. of Belgium. Truncated and extended forms relate to ApoA and ApoE molecules where one or more amino acids are missing or has been added, respectively, at the N and/or C terminal ends of the molecules. Suitably, from two up to eight amino acids are missing or have been added, preferably from three up to six amino acids. Mutated forms relate to ApoA and ApoE molecules where one or more amino acid has been substituted by another amino acid, e.g. ApoA-IM as disclosed in WO-A-93/12143 and WO-A-94/13819. Other mutated forms are ApoA-ISeattle (Deeb et al (1991) J. Bio. Chem. 266:13654–13660), ApoA-IYame (Takada et al (1991) J. Lipid Res. 32: 1275 ff) and a yet unnamed mutated form of ApoA-I (Matsunaga et al (1991) Proc. Natl. Acad. Sci. USA 88:2793–2797).

Known ApoA's are e.g. ApoA-I, ApoA-II and ApoA-IV. In the present invention, suitably, the ApoA is ApoA-I, or analogs thereof. Natural plasma ApoA-I is a single polypeptide chain of 243 amino acids, whose primary sequence is known (Brewer et al. (1978) Biochem. Biophys. Res. Commun. 80: 623–630). The ApoA can also be a mutated form of ApoA-I where at least one Cys residue has been substituted for an amino acid residue, e.g. an Arg residue, making formation of disulfide-linked dimer possible. In the amino acid sequence of natural human ApoA-I, Arg residues are located at positions 10, 27, 61, 83, 116, 123, 131, 149, 151, 153, 160, 171, 173, 177, 188 and 215. Of these, substitutions are preferred at one or more of positions 160, 171, 173, 177 and 188, i.e. at positions within the same α-helix. More preferably, the Arg residue is substituted at positions 171 and/or 173.

Human ApoE and variants thereof are disclosed in "Human Apolipoprotein Mutants MIII", ed. by C. R. Sirtori et al (1993) Nato ASI Series, Springer Verlag, Berlin, II 73:81–96.

The following Examples are provided for purposes of illustration only and are not to be construed as in any way limiting the scope of the present invention, which is defined by the appended claims.

The percentages and parts are per weight, unless otherwise stated.

Experimental

Materials and Equipment

Cohn's fraction IV precipitate was obtained from the Plasma Department of Pharmacia & Upjohn in Stockholm, Sweden.

The chromatography gels used were DEAE-SEPHAROSE® FF and SUPERDEX® 200 prep grade, both of which were obtained from Pharmacia Biotech of Uppsala, Sweden.

Sartoclean CA-filter with pore size 3+0.8 µm from Sartorius in Germany.

All of the chemicals were of analytical reagent grade.

Analytical Methods and Calculations

A radioimmunoassay (RIA) was used for quantitative Apo A-I determination and yield calculations. The procedure has been developed by Mercodia AB of Uppsala, Sweden. The method which is named Mercodia Apolipoprotein A-I RIA is a competitive radio-immunoassay, where apolipoproteins of the sample compete with a fixed amount of $^{125}$I-labeled Apo A-I for the binding sites of specific monoclonal antibodies attached to a solid phase, micro-SEPHAROSE®. After incubation and separation of unbounded proteins the radioactivity is measured in a gamma counter. The radioactivity is inversely proportional to the concentration of apolipoprotein A-I in the sample.

EXAMPLE 1

The effect of various washing and extraction buffer compositions on the yield and purity of Apo A-I as target protein were studied. The starting material was taken from the filter in the fractionation process where Cohn's fraction IV is collected.

The following conditions were used in all tests in Example 1:

1. 6 g of the starting material (filtered fraction IV precipitate and filter aid) was put in test tubes of 50 ml.
2. When a washing buffer was used, it was poured into the tube up to the 50 ml mark and mixed on a rocking machine for three hours. The temperature was +4° C. in all Examples unless otherwise stated. Centrifugation at 500 rpm and 15° C. for 20 min, was used to separate the supernate which was discarded and the rest of the fraction IV mixture was used in the next step.
3. An extraction buffer was poured up to 50 ml, including the fraction IV mixture. The incubation time was two hours at +4° C. on the rocking machine. After centrifugation at 500 rpm and 15° C. for 20 min, the supernate was analyzed to establish the content of Apo A-I.

The results are evident from the following Table.

TABLE I

Influence of washing and extraction buffer compositions on the specific activity and yield of Apo A-I

| Test No. | Washing buffer | Extraction buffer | Total $A_{280}$ | Specific activity (mg Apo A-I/ $A_{280}$) | Apo A-I yield (%) |
|---|---|---|---|---|---|
| WE1 | — | water pH = 2.4 | 715 | 0.0435 | 62 |
| WE2 | water pH = 6 | water pH = 2.4 | 813 | 0.0393 | 64 |
| WE3 | water pH = 6 | 8 M urea | 413 | 0.0963 | 87 |
| WE4 | — | 1 M NaCl, 0.02 M phosphate, 1% TRITON ® X-100 Ph = 4.0 | 54.6 | 0.142 | 15 |
| WE5 | — | 1 M NaCl, 0.02 M phosphate, 1% TRITON ® X-100 pH = 5.3 | 615 | 0.0105 | 13 |
| WE6 | — | 1 M NaCl, 0.02 M phosphate, 1% TRITON ® X-100 pH = 7.5 | 60 | 0.301 | 36 |
| WE7 | — | 0.1 M glycine pH = 3.0 | 784 | 0.0224 | 35 |
| WE8 | 0.2 M NaCl, 0.02 M phosphate, pH = 5.3 | 8 M urea | 592 | 0.0531 | 63 |
| WE9 | 0.02 M NaCl, phosphate, pH = 6.0 | 8 M urea | 523 | 0.0505 | 53 |
| WE10 | 0.2 M NaCl, 0.02M phosphate, pH = 6.5 | 8 M urea | 513 | 0.0517 | 53 |
| WE11 | 0.2 M NaCl, 0.02 M phosphate, pH = 7.0 | 8 M urea | 480 | 0.0542 | 52 |
| WE12 | 0.2 M NaCl, 0.02 M phosphate, pH = 7.5 | 8 M urea | 413 | 0.0517 | 43 |
| WE13 | 0.2 M NaCl, 0.02 M phosphate, pH = 8.0 | 8 M urea | 436 | 0.0526 | 46 |
| WE14 | 1 M NaCl, 0.2 M phosphate, pH = 5.4 | 8 M urea | 863 | 0.0530 | 92 |
| WE15 | 1 M NaCl, 0.2 M phosphate, pH = 6.0 | 8 M urea | 790 | 0.0514 | 81 |
| WE16 | 1 M NaCl, 0.2 M phosphate, pH = 6.5 | 8 M urea | 793 | 0.0491 | 78 |
| WE17 | 1 M NaCl, 0.2 M phosphate, pH = 7.0 | 8 M urea | 728 | 0.0549 | 80 |
| WE18 | 1 M NaCl, 0.2 M phosphate, pH = 7.5 | 8 M urea | 697 | 0.0565 | 79 |
| WE19 | 1 M NaCl, 0.2 M phosphate, pH = 8.0 | 8 M urea | 712 | 0.0532 | 76 |
| WE20 | 0.07 M citric acid, 0.08 M $Na_2HPO_4$, pH = 4.0 | 8 M urea | 279 | 0.165 | 92 |
| WE21 | 0.07 M citric acid, 0.08 M $Na_2HPO_4$, | 8 M urea | 255 | 0.155 | 79 |

TABLE I-continued

Influence of washing and extraction buffer compositions on the specific activity and yield of Apo A-I

| Test No. | Washing buffer | Extraction buffer | Total $A_{280}$ | Specific activity (mg Apo A-I/ $A_{280}$) | Apo A-I yield (%) |
|---|---|---|---|---|---|
| WE22 | pH = 4.0, 20° C. 0.07 M citric acid, 0.08 M Na$_2$HPO$_4$, pH = 4.0 | 20% (v/v) ethanol | 20 | 0.0128 | 1 |
| WE23 | 0.07 M citric acid, 0.08 M Na$_2$HPO$_4$, pH = 4.0 | 40% (v/v) ethanol | 15 | 0.0240 | 1 |
| WE24 | 0.07 M citric acid, 0.08 M Na$_2$HPO$_4$, pH = 4.0 | 60% (v/v) ethanol | 24 | 0.0263 | 1 |

As is evident from Table I, Apo A-I can be prepurified with a wide choice of extraction buffers, However, in order to obtain a high yield in combination with a high specific activity it is preferred to use a washing buffer followed by an extraction buffer containing e.g. urea or TRITON® X-100.

EXAMPLE 2

The purifying effect obtained by precipitating macromolecular impurities followed by filtration was studied using Apo A-I as target protein. The starting material was filtered fraction IV precipitate with a filter aid, washed and extracted in accordance with test WE 20 in Example 1 but on a larger scale. It was further prepurified by precipitation of macromolecular impurities, such as various lipoproteins, with 10% PEG 4000. The precipitation was followed by centrifugation for 15 min at 2,000 rpm and 15° C. Subsequently, the resulting solution was filtered using a Sartoclean CA filter with pore size 3+0.8 µm. The yield of Apo A-I was unaffected by the filtration step. The results after each step are evident from the following Table.

TABLE II

Influence of washing, extraction, PEG precipitation and filtration on the specific activity and yield of Apo A-I

| Test No. | Prepurification step | Total $A_{280}$ | Specific activity (mg Apo A-I/ $A_{280}$) | Apo A-I yield (%) |
|---|---|---|---|---|
| E1 | Washing | 2.18 × 10$^5$ | 0.0170 | 10 |
| E1 | Extraction | 1.65 × 10$^4$ | 0.0856 | 90 |
| E1 | PEG precipitation | 1.19 × 10$^4$ | 0.104 | 90 |
| E1 | Filtration | 8.06 × 10$^3$ | 0.154 | 85 |

As is evident from Table II, the specific activity is almost doubled after PEG precipitation and filtration while the overall Apo A-I yield is essentially maintained throughout the prepurifying sequence. For example only 10% of the initial Apo A-IA is lost in the washing step.

EXAMPLE 3

The purifying effect of an anion-exchange chromatography gel was studied using Apo A-I as target protein. The starting material was retrieved after the filtration step in Example 2. The gel used was a DEAE-SEPHAROSE® Fast Flow.

a) Small-scale Test

Conditions used in the small-scale experiment:

Bed volume: 10.2 ml
Equilibration before sample loading: buffer containing 30 mM Tris, pH=7.5, ionic strength=2.8 mS/cm
Sample loading: buffer characteristics pH=7.5, ionic strength=1.7 mS/cm
Elution 1: 3 column volumes (cv) of equilibration buffer
Elution 2: 2 cv of buffer containing 0.075 M NaCl and 30 mM Tris, pH=7.5, ionic strength=10.7 mS/cm
Elution 3: 5 cv of buffer containing 0.10 M NaCl and 30 mM Tris-HCl, pH=7.5, ionic strength=13.0 mS/cm
Total elution: 4 cv of 2 M NaCl
Sanitation: 5 cv of 1 M NaOH
Pump flow: 6 cv/h The results after each step are given as DEAE 16 in Table III.

b) Large-scale Test

A scale-up experiment of DEAE 16 was performed. A gel volume of 900 ml was used, which means a scale-up of about 90 times. Buffer and sample amounts were adapted to the new gel volume. The experimental conditions used in the scale-up experiment b) were identical to those in the small-scale experiment a) with the following exceptions:

Gel volume: 900 ml
Elution 2: ionic strength=10.3 mS/cm
Elution 3: 3 cv of the buffer
Elution 4: 1 cv of the buffer used in elution 3
Pump flow: 5.1 cv/h The results after each step are given as DEAE 27 in Table III.

TABLE III

Influence of three or four elution steps after binding of Apo A-I to an anion-exchange chromatography gel on the specific activity and yield of Apo A-I

| Test No. | Pre-purification step | Total $A_{280}$ | Specific activity (mg Apo A-I/$A_{280}$) | Apo A-I yield (%) |
|---|---|---|---|---|
| DEAE 16 | Sample loaded | 57.3 | 0.127 | (100) |
| DEAE 16 | Elution 1 | 20.1 | 0.0211 | 5 |
| DEAE 16 | Elution 2 | 5.32 | 0.181 | 13 |
| DEAE 16 | Elution 3 | 9.44 | 0.492 | 64 |
| DEAE 16 | Total elution | 11.4 | 0.0264 | 4 |
| DEAE 27 | Sample loaded | 2,780 | 0.118 | (100) |
| DEAE 27 | Elution 1 | 724 | — | — |
| DEAE 27 | Elution 2 | 271 | 0.159 | 13 |
| DEAE 27 | Elution 3 | 560 | 0.405 | 69 |
| DEAE 27 | Elution 4 | 72.5 | 0.0831 | 1 |
| DEAE 27 | Total elution | 759 | 0.0126 | 2 |

As is evident from Table III, it is possible to use the present invention comprising prepurifying Apo A-I followed by binding of said Apo A-I to an anion-exchange chromatography gel and obtain a purified product with a high specific activity in combination with a high yield. This holds true in small scale as well as on a larger scale.

EXAMPLE 4

The purifying effect of a gel-filtration gel equilibrated with an anionic surfactant was studied using Apo A-I as target protein. Eluate 3 from the scale-up experiment of Example 3 (DEAE 27) was concentrated using a Millipore UF-system with a cut-off of 10 kDa. This concentrated DEAE eluate 3 was used as starting material. For comparison the game starting material was applied to the gel-filtration gel equilibrated without a surfactant.

a) Small-scale Test Without a Compound Capable of Reducing Protein-protein Interactions (Comparative Test)

The gel was SUPERDEX® 200 prep grade; gel volume: 100 ml; bed height: 48 cm.

Equilibration buffer: 0.1 M NaCl and 30 mM Tris, pH=7.5, ionic strength=12.6 mS/cm
Sample loading: 1 ml of the concentrated DEAE eluate 3 with $A_{280}$=2.18 corresponding to a concentration of 0.94 mg Apo A-I/ml
Fraction I was collected
Pump flow: 1 ml/min The results are given as G1 in Table IV.

b) Small-scale Tests with Sodium Dodecyl Sulfate (SDS) in Equilibration Buffer

In this test the bed height was 65 cm. The experimental conditions used in this experiment were identical to those in a) with the following exceptions;

Equilibration buffer: 0.1 M NaCl and 30 mM Tris, 0.1% SDS, pH=7.5, ionic strength=12.6 mS/cm
Sample loading: 0.1 ml DEAE eluate 3 with $A_{280}$=2.18 corresponding to a concentration of 0.94 mg Apo A-I/ml
Fractions 1–4 were collected
Pump flow: 1 ml/min The results are given as G15 in Table IV.

c) Large-scale Test with Sodium Dodecyl Sulfate (SDS) in Equilibration Buffer

The gel-filtration step was scaled up 50 times, which means that a gel volume of 5,000 ml SUPERDEX® was used. The experimental conditions used in the scale-up experiment c) were identical to those in the small-scale experiment b) with the following exceptions:

Sample loading: 48 ml DEAE eluate 3 with $A_{280}$=2.18 corresponding to a concentration of 0.94 mg Apo A-I/ml
Fractions 1–3 were collected
Sanitation: approx. 5 cv 0.5 M NaCl
Pump flow: 1.9 l/h The results are given as G18 in Table IV.

TABLE IV

Influence of an anionic surfactant in equilibration of a gel-filtration gel on the specific activity and yield of Apo A-I

| Test No. | Prepurification step | Total $A_{280}$ | Specific activity (mg Apo A-I/$A_{280}$) | Apo A-I yield (%) |
|---|---|---|---|---|
| G1  | Sample loaded | 2.18  | 0.429  | (100) |
| G1  | Fraction 1    | 1.72  | 0.307  | 56    |
| G15 | Sample loaded | 2.18  | 0.429  | (100) |
| G15 | Fraction 1    | 0.278 | 0.114  | 3     |
| G15 | Fraction 2    | 0.78  | 0.0692 | 6     |
| G15 | Fraction 3    | 1.08  | 0.757  | 87    |
| G15 | Fraction 4    | 0.18  | 0.275  | 5     |
| G18 | Sample loaded | 105   | 0.429  | (100) |
| G18 | Fraction 1    | 13.1  | 0.250  | 7     |
| G18 | Fraction 2    | 30.9  | 0.113  | 8     |
| G18 | Fraction 3    | 57.7  | 0.753  | 97    |

As is evident from Table IV, the preferred embodiment of the present invention where a gel-filtration chromatography step follows the anion-exchange chromatography step, gives an improved specific activity at a high yield of Apo A-I.

What is claimed is:

1. A process for purifying apolipoprotein A (ApoA) or apolipoprotein E (ApoE) from human plasma, comprising obtaining a fraction of human plasma containing said ApoA or ApoE which is obtained by freezing or alcohol precipitation of plasma or serum, prepurifying said fraction in at least one step to remove high molecular weight proteins and fatty compounds, binding said ApoA or ApoE to an anion-exchange chromatography gel, and thereafter eluting said ApoA or ApoE from said anion-exchange chromatography gel.

2. The process of claim 1 wherein the fraction is Cohn Fraction IV.

3. The process of claim 1 wherein the fraction is precipitated by addition of a compound selected from the group consisting of lower aliphatic alcohols, ethers, ammonium sulfate, rivanol (2-ethyl-6-9-diamine acridinelactat), and polyethylene glycol.

4. The process of claim 1 wherein the anion-exchange chromatography gel is selected from the group consisting of DEAE agarose gels and Q agarose gels.

5. The process of claim 1 wherein the pre-purification is done by precipitating the ApoA or ApoE followed by filtration, centrifugation or sedimentation.

6. The process of claim 5 wherein the ApoA or ApoE is precipitated and then washed by addition of an aqueous solution to dissolve impurities.

7. The process of claim 6 wherein the washed ApoA or ApoE is then solubilized by addition of a surfactant.

\* \* \* \* \*